United States Patent [19]

Bohler et al.

[11] 3,970,649
[45] July 20, 1976

[54] BISAZOMETHINE METAL COMPLEXES

[75] Inventors: Hans Bohler, Rheinfelden; Rolf Griesser, Binningen, both of Switzerland

[73] Assignee: Sandoz Ltd., Basel, Switzerland

[22] Filed: May 30, 1975

[21] Appl. No.: 582,100

[30] Foreign Application Priority Data
June 5, 1974    Sweden................................. 747663

[52] U.S. Cl.......................... 260/240 G; 260/270 K; 260/309.2; 260/566 R; 260/576; 260/558 A; 260/429 C
[51] Int. Cl.².......................... C07F 3/06; C07F 1/06; C07F 15/04; C07F 15/06
[58] Field of Search......... 260/240 G, 429 C, 270 K

[56] References Cited
UNITED STATES PATENTS

| | | | |
|---|---|---|---|
| 3,864,371 | 2/1975 | Inman et al. | 260/429 C X |
| 3,875,200 | 4/1975 | L'Eplattenier et al. | 260/429 C X |
| 3,896,113 | 7/1975 | Kaul | 260/240 G |

FOREIGN PATENTS OR APPLICATIONS

| | | | |
|---|---|---|---|
| 39,266 | 12/1970 | Japan | 260/270 K |
| 1,366,800 | 9/1974 | United Kingdom | |

Primary Examiner—Allen B. Curtis
Attorney, Agent, or Firm—Gerald D. Sharkin; Richard E. Vila; Thomas C. Doyle

[57] ABSTRACT

Disclosed are pigment dyes containing the basic structure of formula I,

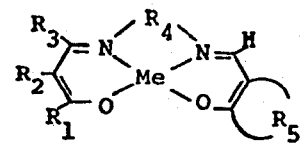

in which $R_1$ is alkyl,
$R_2$ is alkylcarbonyl, alkoxycarbonyl or $-CONR_6R_7$,
$R_3$ is hydrogen or alkyl
$R_4$ is an aromatic carbo- or heterocyclic bivalent radical bound through ortho or peri-positions
$R_5$, together with $>C=C<$ group, signifies an aromatic carbo- or heterocyclic ring,
$R_6$ is hydrogen or alkyl,
$R_7$ is hydrogen, alkyl or a mono- or bi-nuclear aromatic carbo- or heterocyclic ring, and
Me is a bivalent transition metal atom or zinc, their production and use in pigmenting, for example, plastics, synthetic resins, paints, varnishes, paper, viscose and cellulose acetate.

22 Claims, No Drawings

BISAZOMETHINE METAL COMPLEXES

The invention relates to bisazomethine metal complexes.

Thus, the invention provides pigment dyes containing the basic structure of formula I,

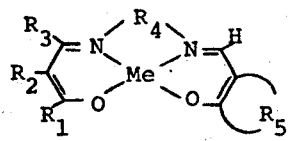
I in which $R_1$ is alkyl,
$R_2$ is alkylcarbonyl, alkoxycarbonyl or $-CONR_6R_7$,
$R_3$ is hydrogen or alkyl
$R_4$ is an aromatic carbo- or heterocyclic bivalent radical bound through ortho or peri-positions
$R_5$, together with the $>C=C<$ group, signifies an aromatic carbo- or heterocyclic ring,
$R_6$ is hydrogen or alkyl,
$R_7$ is hydrogen, alkyl or a mono- or bi-nuclear aromatic carbo- or heterocyclic ring, and
Me is a bivalent transition metal atom or zinc.

The basic structure of formula I may be substituted in any of the aromatic nuclei, and such nuclei may have further nuclei fused thereto, any substituent, however, being chosen so as not deleteriously to affect the pigment properties of the compounds, suitable examples being hereinafter given. The compounds may also bear a carboxy group as one of said substituents. Any alkyl radical or moiety in the basic structure of formula I is preferably of 1 to 4 carbon atoms.

Representative of the compounds provided by the invention are the compounds of formula Ia,

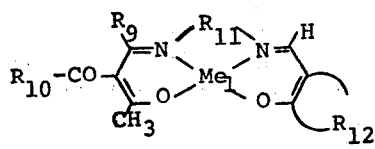
Ia where
$R_9$ is hydrogen or methyl,
$R_{10}$ is $C_{1-2}$alkyl, $C_{1-2}$alkoxy or $-NHR_{13}$, $R_{11}$ is 1,2-phenylene, unsubstituted or substituted as hereinafter set forth, 1,2-, 2,3- or 1,8-naphthylene, 9,10-phenanthrylene, 5,6-acenaphthenylene or a radical of formula (a), (b), (c), (d) or (e),

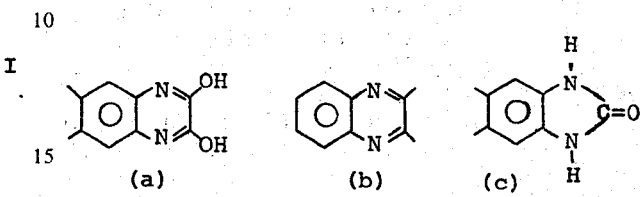

(a)   (b)   (c)

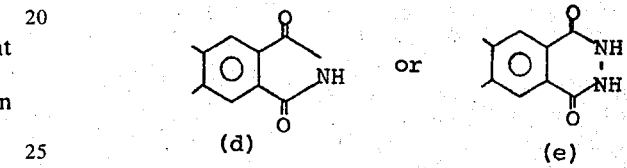

(d)   (e)

$R_{12}$ signifies a radical of formula (f), (g), (h), (i) or (j),

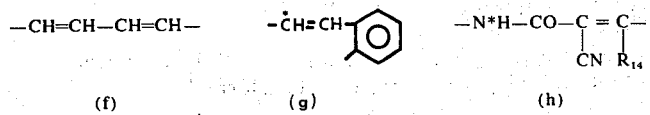

(f)   (g)   (h)

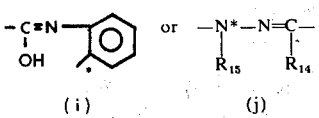

(i)   (j)

wherein
the asterisked atom is bound to the carbon adjacent the oxygen in formula Ia, radicals (f) and (g) being unsubstituted or substituted as hereinafter set forth,
$R_{13}$ signifies hydrogen, $C_{1-4}$alkyl, naphthyl, benzimidazolonyl-5 or phenyl, or phenyl substituted by up to three substituents selected from methyl (up to 3 thereof), chlorine, bromine, nitro and $C_{1-2}$alkoxy (up to 2 thereof), $C_{1-2}$alkylcarbonylamino, phenylcarbonylamino and phenylaminocarbonyl (up to 1 thereof), which latter two radicals are unsubstituted or substituted as hereinafter set forth,
$R_{14}$ is methyl or phenyl,
$R_{15}$ is hydrogen, methyl or phenyl, and
$Me_1$ is nickel, copper, zinc or cobalt, any substituted phenylene as $R_{11}$, any phenylcarbonylamino or phenylaminocarbonyl in $R_{13}$ and any substituted radical (f) or (g) as $R_{12}$ being substituted by up to two substituents selected from chlorine, bromine, methyl and $C_{1-2}$alkoxy (up to two thereof), cyano, hydroxy, nitro, $C_{1-2}$alkoxycarbonyl, aminocarbonyl, $C_{1-2}$alkylaminocarbonyl, di-$C_{1-2}$alkylaminocarbonyl, carboxyl, phenyl and phenoxy (up to 1 thereof).

In the compounds of formula Ia, $R_9$ is preferably hydrogen. Any $C_{1-2}$alkyl as $R_{10}$ is preferably methyl. $R_{13}$ is preferably hydrogen, $C_{1-2}$alkyl, benzimidazolonyl-5 or optionally substituted phenyl, any phenyl as $R_{13}$ preferably being unsubstituted or substituted by up to 3 substituents selected from methyl (up to 3), chlorine, bromine, nitro and $C_{1-2}$alkoxy (up to 2 from this group) and $C_{1-2}$alkylcarbonylamino, phenylcarbonylamino and phenylaminocarbonyl (up to one from this group), any phenyl group in said latter two radicals being unsubstituted or substituted by up to two substituents selected from chlorine, bromine and $C_{1-2}$alkoxy. Preferably $R_{10}$ is unsubstituted benzimidazolonyl-5-amino or phenylamino in which the phenyl is unsubstituted or substituted as indicated above to be preferred. More preferably $R_{10}$ is unsubstituted phenylamino or phenylamino substituted by one or two methoxy groups and/or by a methyl or chlorine. $R_{11}$ is preferably a 1,2-phenylene radical, unsubstituted or substituted by up to two substituents as defined above, a radical of formula (a), above, or a radical of formula (c), above, any 1,2-phenylene preferably being unsubstituted or mono-substituted by chlorine, bromine, methyl, methoxy, or nitro, more preferably being unsubstituted or mono substituted by chlorine, methyl or methoxy.

Where $R_{12}$ signifies an optionally substituted radical of formula (f), such is preferably unsubstituted or substituted by one or two substituents selected from chlorine, bromine and methoxy (up to two thereof) or nitro (up to one thereof). More preferably it is unsubstituted.

Where $R_{12}$ signifies an optionally substituted radical of formula (g), such is preferably of formula (g'),

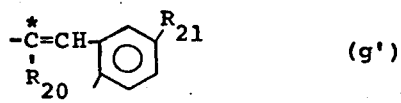

where $R_{20}$ is hydrogen or carboxy and $R_{21}$ is hydrogen, chlorine, bromine or nitro, preferably hydrogen.

Where $R_{12}$ signifies a radical of formula (h), $R_{14}$, therein, is preferably methyl.

Where $R_{12}$ signifies a radical of formula (j), $R_{14}$, therein, is preferably methyl and $R_{15}$, therein, is preferably phenyl.

Of the radicals (f) to (j) as $R_{12}$, the radicals (f), (g), (h) and (i) are more preferred, particularly the radicals (g), (h) and (i).

In the compounds of formula Ia, Me, preferably signifies nickel or copper, most preferably nickel.

As a preferred class of compounds of formula Ia may be given the compounds of formula Ib,

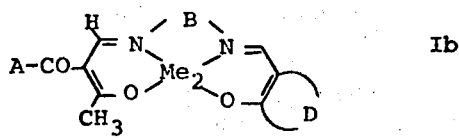

in which

A is methyl, $C_{1-2}$alkoxy, —$NH_2$, $C_{1-2}$alkylamino, benzimidazolonyl-5-amino or phenylamino, said phenylamino being unsubstituted or substituted by up to three substituents selected from methyl (up to 3 thereof), chlorine, bromine, nitro and $C_{1-2}$alkoxy (up to 2 thereof), $C_{1-2}$alkylcarbonylamino, phenylcarbonylamino and phenylaminocarbonyl (up to 1 thereof), the phenyls in said phenylcarbonylamino and phenylaminocarbonyl groups being unsubstituted or substituted by up to two substituents selected from chlorine, bromine and $C_{1-2}$alkoxy, B signifies unsubstituted 2,3-dihydroxyquinoxalinylene-6,7, benzidimazolonylene-5,6 or 1,2-phenylene, or 1,2-phenylene substituted by up to two substituents selected from chlorine, bromine, methyl and $C_{1-2}$alkoxy (up to 2 thereof), cyano, hydroxy, nitro, $C_{1,2}$-alkoxycarbonyl, aminocarbonyl and carboxy (up to 1 thereof), D signifies a radical (f) above, unsubstituted or substituted by up to two substituents selected from chlorine, bromine and methoxy (up to 2 thereof), and nitro (up to 1 thereof); a radical of formula (i), above, a radical of formula (g'), above, a radical of formula (h), in which $R_{14}$ is methyl, or a radical of formula (j), in which $R_{14}$ is methyl and $R_{15}$ is phenyl, and $Me_2$ is nickel or copper.

As a further preferred class of compounds may be given the compounds of formula Ic,

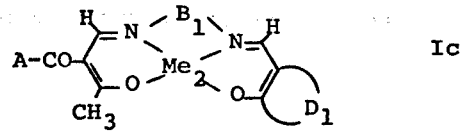

where
$A_1$ is unsubstituted benzimidazolonyl-5-amino, unsubstituted phenylamino or phenylamino substituted by up to three substituents selected from methyl (up to 3 thereof), chlorine, bromine, nitro, $C_{1-2}$alkoxy (up to 2 thereof), $C_{1-2}$alkylcarbonylamino, phenylcarbonylamino and phenylaminocarbonyl (up to 1 thereof), any phenyl moiety in said latter two radicals being unsubstituted or substituted by up to two substituents selected from chlorine, bromine and $C_{1-2}$alkoxy, $B_1$ signifies unsubstituted benzimidazolonylene-5,6, or 1,2-phenylene, unsubstituted or mono-substituted by chlorine, bromine, methyl, methoxy or nitro, $D_1$ signifies an unsubstituted radical (f), above, a radical (g'), above, where $R_{21}$ is hydrogen, a radical (h), above, where $R_{14}$ is methyl, or a radical (i), above, and $Me_2$ is as defined above.

As a still further preferred class of compounds may be given in the compounds of formula Id,

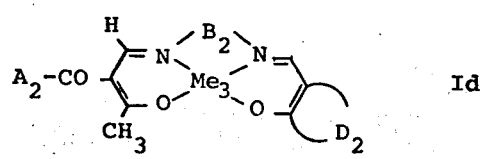

where
- $A_2$ is phenylamino, unsubstituted or substituted by one or two methoxy groups and/or by a chlorine or methyl,
- $B_2$ is unsubstituted benzimidazolonylene-5,6, or 1,2-phenylene, unsubstituted or mono-substituted by chlorine, methyl or methoxy,
- $D_2$ is a radical (g'), above, in which $R_{21}$ is hydrogen, a radical (h), above, where $R_{14}$ is methyl, or a radical (i), above, and
- $Me_3$ is nickel.

Where, in formula Id, $A_2$ is phenylamino substituted by two methoxy groups, such are preferably in positions 2 and 5 of the phenyl ring. Any single methoxy substituent is preferably in position 2 of said ring.

The invention also provides a process for the production of pigment dyes containing the basic structure of formula I, above, which process comprises a) metallizing a compound having the basic structure of formula II,

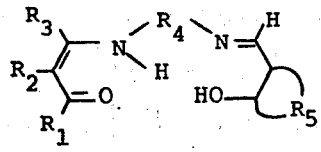

in which $R_1$ to $R_5$ are as defined above,
by reaction with a salt of a bivalent transition metal or of zinc, or b) condensing a diamine of formula III,

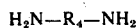

where $R_4$ is as defined above,
with an ortho-hydroxyaldehyde of formula IV,

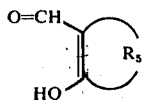

in which $R_5$ is as defined above,
and with a compound of formula V

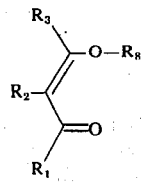

in which
- $R_1$ to $R_3$ are as defined above, and
- $R_8$ is alkyl (preferably of 1 to 4 carbon atoms) or hydrogen, in the presence of a salt of a bivalent transition metal or of zinc, or c) condensing an ortho-hydroxyaldehyde of formula IV, with a compound of formula VI,

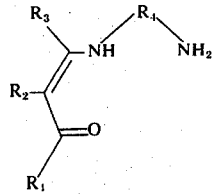

in which $R_1$ to $R_4$ are as defined above,
in the presence of a salt of a bivalent transition metal or of zinc.

The preferred transition metal and zinc salts employed in the above processes (a), (b) and (c) are the hydrosoluble salts, e.g. the chlorides, sulphates, nitrates, formates and acetates, the latter being especially preferred.

The metallisation reaction in process (a) may be carried out in conventional manner, e.g. with the compound of formula II dissolved in a solvent, e.g. in N,N-dimethyl formamide, or in suspension form. The compounds of formula II have low solubility in water, alcohols, ketones and hydrocarbons.

The condensation reaction in processes (b) and (c) is conveniently carried out in conventional manner. Suitably, condensation is carried out in an inert solvent, e.g. in water, an alcohol, glycol or glycol ether containing up to 4 carbon atoms, or in dimethylformamide. A suitable temperature is from 20° to 150°C, preferably from 40° to 100°C.

The resulting products may be isolated and purified in conventional manner, isolation conveniently being effected by precipitation from reaction media in which the products are insoluble. Where dimethylformamide is employed as reaction medium, precipitation is conveniently effected by adding water to the hot medium until a turbid solution forms, followed by cooling and filtration.

The compounds of formula II are new and form a further aspect of the present invention. They may be obtained employing process (b) or (c), above, in the absence of the transition metal or zinc salt.

The compounds of formula VI are also new and form a further aspect of the invention. They may be produced by condensing a compound of formula III, above, with a compound of formula VII,

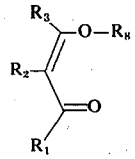

in which $R_1$ to $R_3$ and $R_8$ are as defined above.

The above processes for producing compounds II and VI are conveniently carried out under the same conditions as processes (b) and (c).

The pigments of formula I are suitable for pigmenting plastics or synthetic resins in the mass, (e.g. polyethylene, polystyrene, p.v.c. and synthetic leathers), either free from or containing solvents. They may also be employed as pigments in paints, of an oil or water base, in varnishes, for spin dyeing viscose or cellulose acetate, and for pigmenting rubber. They may also be used in printing in the graphical trade, for mass dyeing of paper, for coating textiles, and for pigment printing.

The dyeings obtained have notable fastness to heat, light, weathering, migration and solvents, and have a good depth of colour. The compounds have good application properties, e.g. resistance to flocculation and crystallisation and good dispersibility and covering capacity.

The pigment properties may be further improved by treatment of the crude pigments in organic solvents at elevated temperatures, e.g. 110° to 200°C. The organic solvents (in which the pigments themselves are not dissolved) may be, for example, chlorobenzenes (mixtures), nitrobenzene, dimethylformamide, glacial acetic acid, ethylene glycol or quinoline.

In the following Examples, the parts and percentages are by weight and the temperatures in degrees centigrade.

EXAMPLE 1

24.6 Parts of 5,6-diaminobenzimidazolone are suspended in 190 parts of boiling methanol. To this mixture 35 parts of α-ethoxymethylene-acetoacetanilide, dissolved in 240 parts of warm methanol, are added slowly and with stirring. The suspension is boiled at reflux for 6 hours, cooled, and the residue filtered off and washed with ethanol. After drying in a vacuum at 70°, the yellow product of formula

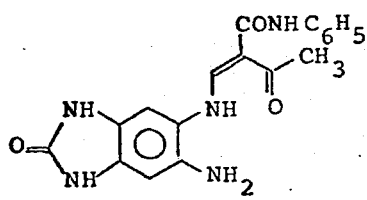

is obtained in good yields.

17.6 Parts of the above product are dissolved in 140 parts of N,N-dimethyl formamide at 90°. A solution of 8.6 parts of 2-hydroxy-1-naphthaldehyde in 50 parts of N,N-dimethyl formamide are slowly added, the mixture is heated to 130° over the course of 3 hours with stirring, cooled to 5° and the obtained precipitate is filtered off, washed with N,N-dimethyl formamide and ethanol and dried at 70° in a vacuum. The yellow product of formula

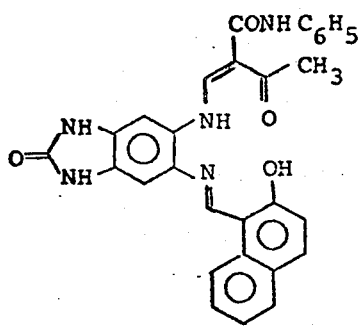

has a M.P. of 297°–298° with decomposition.

7.6 Parts of this product are heated to 130° in 75 parts of N,N-dimethyl formamide. 4 Parts of nickel acetate tetrahydrate in 85 parts of N,N-dimethyl formamide are added dropwise with stirring, heated to 130° and the suspension is stirred at 130°–140° over the course of 4 hours. After cooling the mixture is filtered off and washed with N,N-dimethyl formamide and subsequently with ethanol until the ethanol filtrate is colourless. After drying in a vacuum at 70°, a red pigment of forumla

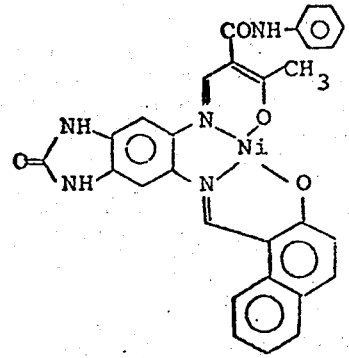

is obtained which in varnishes and PVC gives red dyeings with good fastness properties.

EXAMPLE 2

Following Example 1 but using 3.2 parts of copper acetate-monohydrate in place of nickel acetate tetrahydrate, the brown copper complex of analogous structure is obtained.

EXAMPLE 3

Replacing in Example 1 the 2-hydroxy-1-naphthaldehyde by an equimolar amount of 3-cyano-2,6-dihydroxy-5-formyl-4-methyl-pyridine, a product of formula

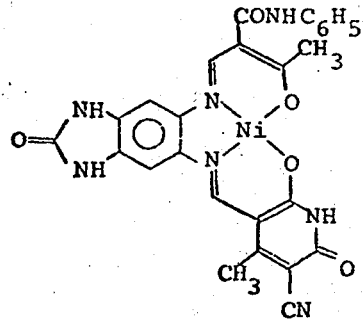

is obtained in similar manner. In varnishes and PVC it shows fast reddish brown dyeings.

EXAMPLE 4

Replacing, in Example 1, the 5,6-diaminobenzimidazolone by 16.2 parts of o-phenylene diamine, a product of formula

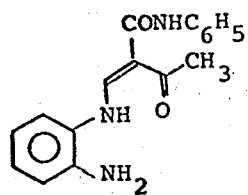

is obtained in analogous manner as intermediate product.

8.9 Parts of this product are dissolved with heating in 640 parts of ethanol. A suspension of 5.3 parts of 3-cyano-2,6-dihydroxy-5-formyl-4-methyl-pyridine in 200 parts of ethanol are slowly added and the mixture is heated to the boil. After stirring for 30 minutes at reflux, 7.5 parts of nickel acetate tetrahydrate in 280 parts of ethanol are slowly added. The reaction mixture is stirred at reflux for 6 further hours, cooled, filtered off by suction and washed with ethanol. After drying at 70° in a vacuum, an orange-yellow pigment of formula

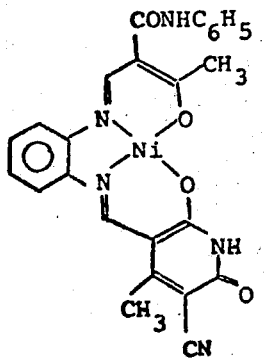

is obtained which has good fastness properties in varnishes and PVC.

EXAMPLE 5

Replacing, in Example 4, the α-ethoxymethyleneacrylonitrile by 2,5-dimethoxy-α-ethoxymethyleneacetoacetanilide, a yellow pigment of formula

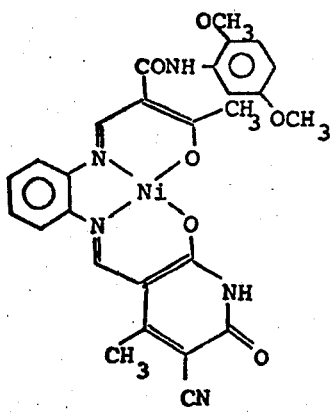

is obtained which in varnishes and PVC has good fastness properties.

EXAMPLE 6

A solution of 35.6 parts of 3-cyano-2,6-dihydroxy-5-formyl-4-methylpyridine in 145 parts of dimethyl formamide is slowly added to a solution of 21.6 parts of o-phenylenediamine in 140 parts of dimethyl formamide. The mixture is subsequently stirred at boiling temperature over the course of 3 hours, cooled and the precipitate is filtered off, washed with ethanol and dried at 80° in a vacuum. The resulting product of formual

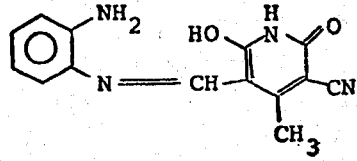

has a M.P. of 271°–274° with decomposition.

A solution of 11.7 parts of α-ethoxymethyleneacetoacetanilide in 40 parts of dimethyl formamide is slowly added at 100° to a suspension of 13.4 parts of the above compound in 95 parts of dimethyl formamide. The mixture is heated to 100°, stirred at this temperature over the course of 30 minutes, and a solution of 12.5 parts of nickel acetate tetrahydrate in 115 parts of dimethyl formamide is slowly added. The reaction mixture is stirred at 120° for 3 hours. After cooling, the precipitate is filtered off, washed with ethanol and dried. The product is identical with the product of Example 4.

APPLICATION EXAMPLE 0.5 Parts of the pigment, obtained in accordance with Example 1, and 5 parts of titanium dioxide pigment are added to a mixture consisting of
   63 parts of a polyvinyl chloride emulsion,
   32 parts of dioctyl phthalate,
   3 parts of a commercial epoxy softener,
   1.5 parts of a commercial stabilizer (barium-cadmium complex)
   0.5 parts of a commercial chelator
and the whole is intimately mixed. The mixture is rolled at 160° for 8 minutes in a roller mill with friction rollers (one roller rotates at 20 r.p.m., the second at 25 r.p.m.) to obtain a better distribution of the pigment. The mixture is subsequently extruded as a film of 0.3 mm thickness. The film is pigmented in a red shade. The dyeing has good fastness to light and migration, and heat resistance.

In the following Table further pigments of formula Ia are indicated which may be produced in analogy with the operating processes of Examples 1 to 6. In all the Examples $R_9$ is hydrogen, except in Example 50 where it is methyl.

TABLE

| Exp. No. | $R_{10}$ | $R_{11}$ | $R_{12}$ | $Me_1$ | Shade in PVC |
|---|---|---|---|---|---|
| 7 | —NHC₆H₅ | ⌬ | -CH=CH-⌬ | Ni | orange |
| 8 | " | O₂N-⌬ |  | " | " |
| 9 | -NH-⌬(NH,NH,CO) | ⌬ |  | " | reddish yellow |

TABLE-continued
| Exp. No. | R₁₀ | R₁₁ | R₁₂ | Me₁ | Shade in PVC |
|---|---|---|---|---|---|
| 10 |  | " | " | " | orange |
| 11 | " | " | —CH=CH—CH=CH— | " | reddish yellow |
| 12 | —NHC₆H₅ | " | 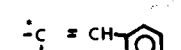 | " | orange |
| 13 | " | " |  | " | yellow |
| 14 | 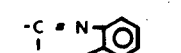 | " | " | " | reddish yellow |
| 15 | 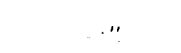 |  | —N*—N=C—<br>   $\|$    $\|$<br>   C₆H₅  CH₃ | Ni | yellow brown |
| 16 | —NHC₆H₅ | " | " | " | " |
| 17 | " | " | —C=C—CO—NH*—<br>  $\|$   $\|$<br>  CH₃ CN | Cu | " |
| 18 | " |  | " | Ni | orange |
| 19 | " |  | " | " | " |
| 20 | " | 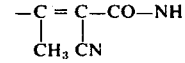 | " | " | reddish yellow |
| 21 | " |  | " | " | orange |
| 22 | 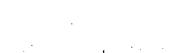 |  | " | " | yellow |
| 23 |  | " | " | " | reddish yellow |
| 24 |  |  | " | Ni | " |
| 25 |  | " | " | " | " |
| 26 |  | " | " | " | " |
| 27 |  | " | " | " | " |
| 28 |  | " | " | " | " |
| 29 |  | " | " | " | " |
| 30 |  | " | " | " | " |
| 31 | —CH₃ |  | " | " | " |

TABLE-continued

| Exp. No. | $R_{10}$ | $R_{11}$ | $R_{12}$ | $Me_1$ | Shade in PVC |
|---|---|---|---|---|---|
| 32 | $-OCH_3$ | " | " | " | " |
| 33 | $-OC_2H_5$ | " | " | " | " |
| 34 | $-NH_2$ | " | " | " | " |
| 35 | $-NHC_6H_5$ | 3,4-dimethylphenyl | " | Ni | " |
| 36 | $-NH-C_6H_4-CH_3$ | 2-methoxyphenyl | " | " | " |
| 37 | $-NHC_6H_5$ | 4-HOCO-phenyl | $-CH=CH-C_6H_5$ | " | orange |
| 38 | " | 4-Cl-phenyl | " | " | " |
| 39 | $-NH-(3-H_3CO, 4-OCH_3)$-phenyl | phenyl | " | " | red |
| 40 | $-NH-(2,4-dinitro)$-phenyl | 4-HO-phenyl | $-C(OCH_3)=CH-CH=CH-$ | " | reddish yellow |
| 41 | $-NH-(2,4,6-trimethyl)$-phenyl | 4-NC-phenyl | $-C^*H=CH-C(NO_2)=CH-$ | " | " |
| 42 | $-NH-(2-OC_2H_5)$-phenyl | 4-$H_2NCO$-phenyl | $-C^*(Cl)=CH-C(Cl)=CH-$ | " | " |
| 43 | $-NH-C_6H_4-CONH-(2-OC_2H_5)$-phenyl | 4-$H_5C_2OCO$-phenyl | $-CH=CH-C_6H_4-Cl$ | Ni | " |
| 44 | $-NH-C_6H_4-CONH-(3-H_3CO,4-OCH_3,5-Br)$-phenyl | 3,5-Br_2-phenyl | $-CH=CH-C_6H_4-OCH_3$ | " | " |
| 45 | $-NH-C_6H_4-NHCO-(3,4-Cl_2)$-phenyl | 4-$H_5C_2O$-phenyl | $-CH=CH-C_6H_4-NO_2$ | " | " |
| 46 | $-NHCH_3$ | benzimidazolone-type | $-C(Cl)=CH-CH=CH-$ | " | " |
| 47 | $-NHC_2H_5$ | " | $-C(Br)=CH-CH=CH-$ | " | " |
| 48 | $-NH-(2,6-Br_2)$-phenyl | 4-$H_3COCO$-phenyl | $-C(CH_3)=C(CN)-CO-NH^*-$ | " | " |
| 49 | $-NH-C_6H_4-NHCOC_2H_5$ | 4-$H_3CO$-phenyl | " | " | " |
| 50 | $-NHC_6H_5$ | benzimidazolone-type | " | " | " |

What is claimed is:
1. A compound of formula I,

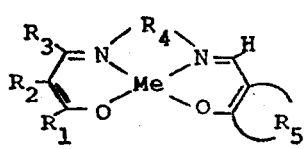

in which
R$_1$ is alkyl,
R$_2$ is alkylcarbonyl, alkoxycarbonyl or -CONR$_6$R$_7$,
R$_3$ is hydrogen or alkyl
R$_4$ is an aromatic carbo- or heterocyclic bivalent radical bound through ortho or peri-positions
R$_5$, together with the >C=C< group, signifies an aromatic carbo- or heterocyclic ring,
R$_6$ is hydrogen or alkyl,
R$_7$ is hydrogen, alkyl or a mono- or bi-nuclear aromatic carbo- or heterocyclic ring, and where
R$_9$ is hydrogen or methyl,
R$_{10}$ is C$_{1-2}$alkyl, C$_{1-2}$alkoxy or -NHR$_{13}$,

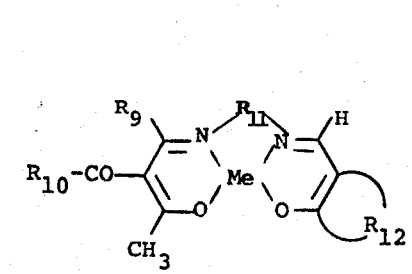

R$_{11}$ is 1,2-phenylene, unsubstituted or substituted as hereinafter set forth, 1,2-, 2,3- or 1,8-naphthylene, 9,10-phenanthrylene, 5,6-acenaphthenylene or a radical of formula (a), (b), (c), (d) or (e),

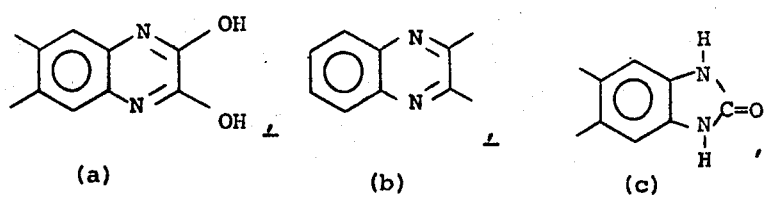

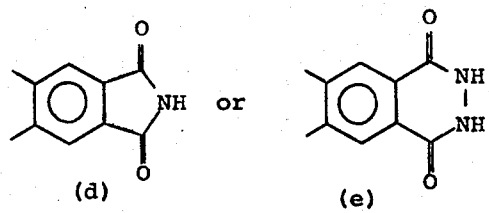

Me is a bivalent transition metal atom or zinc.
2. A compound of claim 1, of formula Ia, R$_{12}$ signifies a radical of formula (f), (g), (h), (i) or (j),

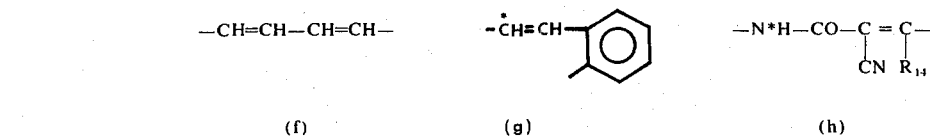

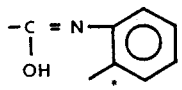

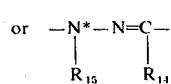

wherein
the asterisked atom is bound to the carbon adjacent the oxygen in formula Ia, radicals (f) and (g) being unsubstituted or substituted as hereinafter set forth, $R_{13}$ signifies hydrogen, $C_{1-4}$alkyl, naphthyl, benzimidazolonyl-5 or phenyl, or phenyl substituted by a total of up to three substituents of which up to 3 are methyl, 2 are selected from chlorine, bromine, nitro and $C_{1-2}$alkoxy and up to 1 is selected from $C_{1-2}$alkylcarbonylamino, phenylcarbonylamino and phenylaminocarbonyl, which latter two radicals are unsubstituted or substituted as hereinafter set forth, $R_{14}$ is methyl or phenyl, $R_{15}$ is hydrogen, methyl or phenyl, and $Me_1$ is nickel, copper, zinc or cobalt, any substituted phenylene as $R_{11}$, any phenylcarbonylamino or phenylaminocarbonyl in $R_{13}$ and any substituted radical (f) or (g) as $R_{12}$ being substituted by a total of up to two substituents of which up to 2 are selected from chlorine, bromine, methyl and $C_{1-2}$alkoxy and up to 1 is selected from cyano, hydroxy, nitro, $C_{1-2}$alkoxycarbonyl, aminocarbonyl, $C_{1-2}$alkylaminocarbonyl, di-$C_{1-2}$alkylaminocarbonyl, carboxyl, phenyl and phenoxy.

3. A compound of claim 2, of formula Ib,

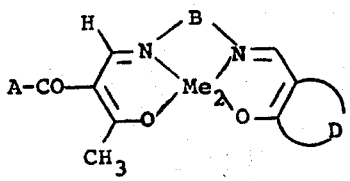

in which
A is methyl, $C_{1-2}$alkoxy, —NH$_2$, $C_{1-2}$alkylamino, benzimidazolonyl-5-amino or phenylamino, said phenylamino being unsubstituted or substituted by a total of up to three substituents of which up to 3 are methyl, up to 2 are selected from chlorine, bromine, nitro and $C_{1-2}$alkoxy and up to 1 is selected from $C_{1-2}$alkylcarbonylamino, phenylcarbonylamino and phenylaminocarbonyl, the phenyls in said phenylcarbonylamino and phenylaminocarbonyl groups being unsubstituted or substituted by up to two substituents selected from chlorine, bromine and $C_{1-2}$alkoxy, B signifies unsubstituted 2,3-dihydroxyquinoxalinylene-6,7, benzidimazolonylene-5,6 or 1,2-phenylene, or 1,2-phenylene substituted by a total of up to two substituents of which up to 2 are selected from chlorine, bromine, methyl and $C_{1-2}$alkoxy and up to 1 is selected from cyano, hydroxy, nitro, $C_{1-2}$alkoxycarbonyl, aminocarbonyl and carboxy, D signifies a radical (f), unsubstituted or substituted by up to two substituents of which up to 2 are selected from chlorine, bromine, and methoxy and up to 1 is nitro; a radical (g'),

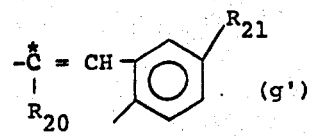

where
$R_{20}$ is hydrogen or carboxy, and
$R_{21}$ is hydrogen, chlorine, bromine or nitro;
a radical (i); in which $R_{14}$ is methyl; or a radical (j), in which $R_{14}$ is methyl and $R_{15}$ is phenyl, and $Me_2$ is nickel or copper.

4. A compound of claim 3, of formula Ic,

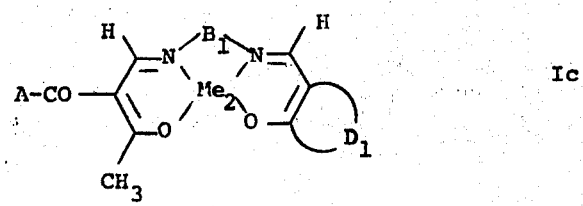

where
$A_1$ is unsubstituted benzimidazolonyl-5-amino, unsubstituted phenylamino or phenylamino substituted by a total of up to three substituents of which up to 3 are methyl, up to 2 are selected from chlorine, bromine, nitro, $C_{1-2}$alkoxy and up to 1 is $C_{1-2}$alkylcarbonylamino, phenylcarbonylamino and phenylaminocarbonyl, any phenyl moiety in said latter two radicals being unsubstituted or substituted by up to two substituents selected from chlorine, bromine and $C_{1-2}$alkoxy, $B_1$ signifies unsubstituted benzimidazolonylene-5,6 or 1,2-phenylene, unsubstituted or mono by chlorine, bromine, methyl, methoxy and nitro, and $D_1$ is an unsubstituted radical (f); a radical (g'), in which $R_{21}$ is hydrogen; a radical (h), where $R_{14}$ is methyl; or a radical (i).

5. A compound of claim 4, of formula Id,

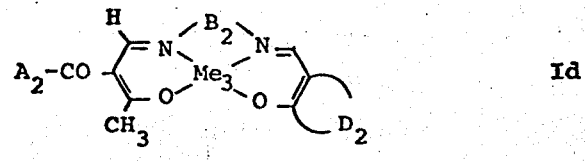

where
$A_2$ is phenylamino, unsubstituted or substituted by one or two methoxy groups and/or by a chlorine or methyl, $B_2$ is unsubstituted benzimidazolonylene-5,6 or 1,2-phenylene, unsubstituted or mono-substituted by chlorine, methyl or methoxy, $D_2$ is a radical (g'), in which $R_{21}$ is hydrogen; a radical (h), in which $R_{14}$ is methyl; or a radical (i), and $Me_3$ is nickel.

6. A compound of claim 5, of formula

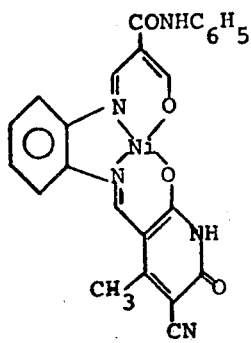

7. A compound of claim 5, of formula

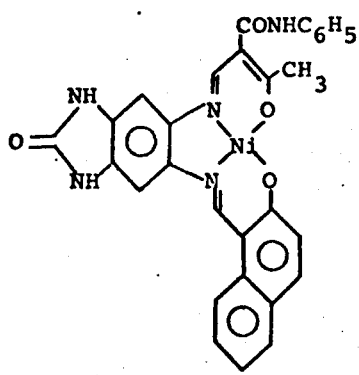

8. A compound of claim 5, of formula

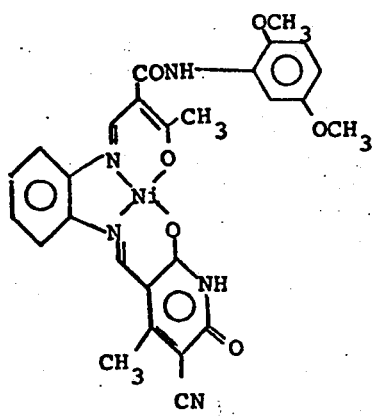

9. A compound of claim 5, of formula

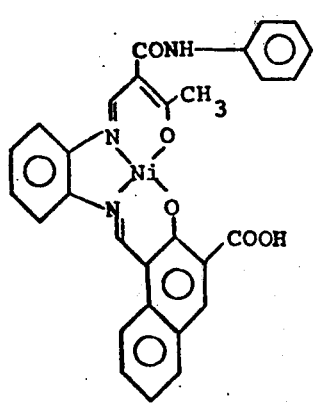

10. A compound of claim 5, of formula

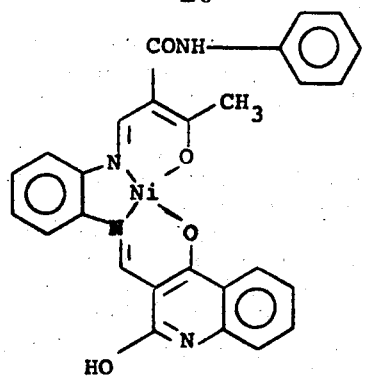

11. A compound of claim 5, of formula

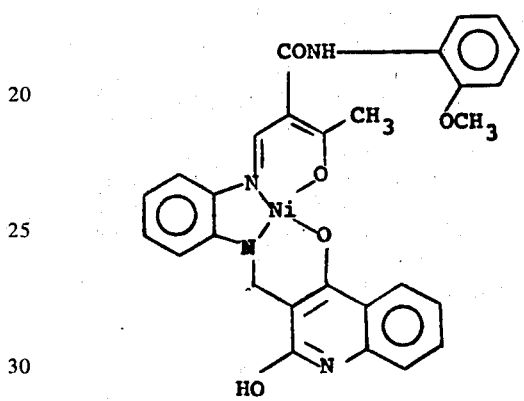

12. A compound of claim 5, of formula

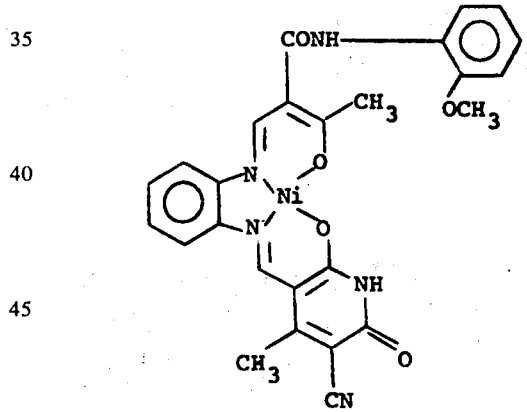

13. A compound of claim 3, wherein A is phenylamino, unsubstituted or substituted.

14. A compound of claim 3, wherein A is benzimidazolonyl-5-amino.

15. A compound of claim 3, wherein B is 1,2-phenylene, unsubstituted or substituted.

16. A compound of claim 3, wherein B is unsubstituted benzimidazolonylene-5,6.

17. A compound of claim 3, wherein D is a radical (f),.

18. A compound of claim 3, wherein D is a radical (g').

19. A compound of claim 3, wherein D is a radical (i).

20. A compound of claim 3, wherein D is a radical (h).

21. A compound of claim 3, wherein D is a radical (j).

22. A compound of claim 3, in which $Me_2$ is nickel.

* * * * *